United States Patent [19]

Iwane et al.

[11] Patent Number: 5,196,598
[45] Date of Patent: Mar. 23, 1993

[54] PROCESS FOR PRODUCING POLYHYDROPEROXY AROMATIC COMPOUND

[75] Inventors: Hiroshi Iwane; Takahiro Sugawara; Naoki Suzuki; Kimiko Kaneko, all of Ibaraki, Japan

[73] Assignee: Mitsubishi Petrochemical Co., Ltd., Tokyo, Japan

[21] Appl. No.: 779,053

[22] Filed: Oct. 18, 1991

[30] Foreign Application Priority Data

Oct. 25, 1990 [JP] Japan ................... 2-288139

[51] Int. Cl.$^5$ ............................. C07C 409/08
[52] U.S. Cl. ................... 568/575; 568/565; 568/569; 568/573; 568/574; 568/577
[58] Field of Search ............ 568/564, 565, 573, 574, 568/575, 577, 569

[56] References Cited

U.S. PATENT DOCUMENTS

| | | | |
|---|---|---|---|
| 2,664,447 | 12/1953 | Lorand et al. | 568/565 |
| 2,664,448 | 12/1953 | Lorand et al. | 568/565 |
| 4,288,637 | 9/1981 | Matsunaga et al. | 568/575 |
| 4,503,262 | 3/1985 | Gupton et al. | |

FOREIGN PATENT DOCUMENTS

| | | |
|---|---|---|
| 0018803 | 11/1980 | European Pat. Off. . |
| 1048013 | 12/1953 | France . |
| 665897 | 1/1952 | United Kingdom . |

*Primary Examiner*—Werren B. Lone
*Attorney, Agent, or Firm*—Oblon, Spivak, McClelland, Maier & Neustadt

[57] ABSTRACT

A process for producing a polyhydroperoxy aromatic compound by oxidation of an aromatic hydrocarbon, e.g., 4,4'-diisopropylbiphenyl and 4,4'-diisopropylnaphthalene, with molecular oxygen is disclosed, in which the oxidation is carried out in the presence of a metal ion selected from cobalt, nickel, zinc and lead ions. Even in using a reaction apparatus made of an iron-containing metal generally employed in industry, a high conversion of secondary alkyl groups can be reached, and the desired polyhydroperoxy aromatic compound can be obtained in a high yield.

12 Claims, No Drawings

PROCESS FOR PRODUCING POLYHYDROPEROXY AROMATIC COMPOUND

FIELD OF THE INVENTION

This invention relates to a process for producing polyhydroperoxy aromatic compounds. More particularly, it relates to a process for producing polyhydroperoxy aromatic compounds by oxidizing aromatic hydrocarbons having two or more secondary alkyl substituents, such as diisopropylbenzene, diisopropylnaphthalene, and diisopropylbiphenyl, with molecular oxygen.

Oxidation of aromatic hydrocarbons having two or more secondary alkyl substituents per molecule, e.g., p-diisopropylbenzene, with molecular oxygen produces p-diisopropylbenzene dihydroperoxide. The resulting dihydroperoxide is acid-decomposed in the presence of an acid catalyst to produce hydroquinone useful as a starting material of an antioxidant or a photographic chemical. Further, 2,6-dihydroxynaphthalene obtained from 2,6-diisopropylnaphthalene and 4,4'-dihydroxybiphenyl obtained from 4,4'-diisopropylbiphenyl are useful as a starting material of liquid crystal polymers, heat-resistant resins, etc.

BACKGROUND OF THE INVENTION

A number of processes for producing compounds having a hydroperoxide group by oxidation of aromatic hydrocarbons substituted with an isopropyl group are known. There are, for example, a process for producing hydroquinone from p-diisopropylbenzene via p-diisopropylbenzene dihydroperoxide (see JP-A-48-72144, the term "JP-A" as used herein means an "unexamined published Japanese patent application"), a process for producing 2,6-dihydroxynaphthalene from 2,6-diisopropyl-naphthalene via 2,6-diisopropylnaphthalene dihydroperoxide (see JP-A-61-93156), and a process for producing 4,4'-dihydroxy-biphenyl from 4,4'-diisopropylbiphenyl via 4,4'-diisopropyl-biphenyl dihydroperoxide (see JP-A-64-75440).

In the working examples disclosed in the above-mentioned publications, the reaction is carried out in a reaction vessel made of Hastelloy B or C. Should the same reaction be performed in a reaction vessel, the part of which in contact with the reaction mixture is made of an iron-containing metal, which is cheaper than that made of Hastelloy and is generally employed in productive industry, the reaction is virtually suspended in its course, and the conversion of the secondary alkyl group does not increase any more.

SUMMARY OF THE INVENTION

An object of the present invention is to provide a process for producing a polyhydroperoxy aromatic compound in high yield while achieving a high conversion of the secondary alkyl groups even by use of a reaction apparatus made of an iron-containing metal generally employed in industry.

The inventors have conducted extensive investigation on production of a polyhydroperoxy aromatic compound by oxidizing an aromatic hydrocarbon having two or more secondary alkyl groups, such as diisopropylbenzene, diisopropylnaphthalene, and diisopropylbiphenyl, with molecular oxygen and, as a result, found that the above-mentioned reaction inhibition can be prevented even in using a reaction vessel made of an iron-based metal by incorporating a specific metal ion into the reaction system, thereby achieving improved conversion and excellent selectivity. The present invention has been completed based on this finding.

That is, the present invention relates to a process for producing a polyhydroperoxy aromatic compound comprising oxidizing a poly-secondary alkyl-substituted aromatic hydrocarbon with the secondary alkyl groups on carbon atoms that are not adjacent to each other on the aromatic ring thereof, wherein a reaction apparatus with its part in contact with a reaction liquid comprising a metal containing 10% by weight or more of iron is used, and the reaction is carried out in the presence of a metal ion selected from a cobalt ion, a nickel ion, a zinc ion, and a lead ion.

DETAILED DESCRIPTION OF THE INVENTION

The poly-secondary alkyl-substituted aromatic hydrocarbon which is used as a starting material in the present invention is an aromatic hydrocarbon substituted with at least 2, and preferably 2 to 4, secondary alkyl groups.

The aromatic nucleus of the aromatic hydrocarbon comprises from 1 to 8, and preferably from 1 to 4, aromatic rings. Specific examples of such an aromatic nucleus are benzene, naphthalene, anthracene, biphenyl, terphenyl, and binaphthalene.

The secondary alkyl groups on the aromatic nucleus include those having from 3 to 9, and preferably from 3 to 7, carbon atoms. Specific examples are isopropyl, 1-methylpropyl, 1-ethylpropyl, 1-methylbutyl, 1-ethylbutyl, and 1-propylbutyl groups.

The two or more substituents of the secondary alkyl-substituted aromatic hydrocarbon must not be on the ringforming carbon atoms which are adjacent to each other.

Specific examples of such hydrocarbons are m- or p-diisopropylbenzene, m- or p-di-sec-butylbenzene, 1,3,5-triisopropylbenzene, 2,6-diisopropylnaphthalene, 2,7-diisopropylnaphthalene, 1,4-diisopropylnaphthalene, 1,5-diisopropylnaphthalene, 2,6-di-sec-butylnaphthalene, 4,4,-diisopropylbiphenyl, 3,3'-diisopropylbiphenyl, 3,4'-diisopropylbiphenyl, 3,5-diisopropylbiphenyl, 4,4'-sec-butylbiphenyl, 4,4''-diisopropylterphenyl, 3,3''-diisopropylterphenyl, 3,4''-diisopropylterphenyl, and 6,6'-diisopropyl-1,1-binaphthalene. Preferred among them are m- or p-diisopropylbenzene, 2,6- or 2,7-diisopropylnaphthalene, and 4,4'-diisopropylbiphenyl.

The reaction vessel to be used is not limited in form but is made of an iron-containing metal. The term "iron-containing metal" as used herein means a metal containing 10% or more of iron, such as carbon steel, stainless steel, cast iron, and Hastelloy A.

The oxidation reaction of the aromatic hydrocarbon with molecular oxygen is generally conducted in a basic aqueous solvent.

Suitable basic compounds to be used include alkali metal compounds, such as alkali metal hydroxides, e.g., sodium hydroxide, potassium hydroxide, and lithium hydroxide; alkali metal carbonates, e.g., sodium carbonate and potassium carbonate; alkali metal hydrogen carbonates, e.g., sodium hydrogen carbonate and potassium hydrogen carbonate; alkali metal phosphates, e.g., sodium phosphate, potassium phosphate, sodium hydrogen phosphate, potassium hydrogen phosphate, sodium dihydrogen phosphate, and potassium dihydrogen phosphate; and alkali metal borates, e.g., sodium tetraborate. These basic compounds may be used either individually or as a mixture of two or more thereof at an arbitrary mixing ratio.

A preferred concentration of the above-mentioned alkali metal compound in an aqueous solvent is 30% by weight or less.

The basic aqueous solvent is used in an amount sufficient to maintain the reaction mixture at a pH of 8 or higher. More specifically, such an amount ranges from 0.1 to 10 parts by weight, and preferably from 0.3 to 5 parts by weight, per part by weight of the aromatic hydrocarbon. If it is less than 0.1 part by weight, oxidation does not sufficiently proceed. Amounts exceeding 10 parts by weight bring no further effects, only resulting in an increase of a basic waste water.

Metallic compounds which can be used for supplying a metal ion selected from cobalt, nickel, zinc, and lead ions are not particularly limited as long as they dissociate into ions in a basic aqueous solvents.

Example of suitable cobalt compounds includes cobalt acetate, cobalt acetylacetonate, ammonium cobalt sulfate, cobalt benzoate, cobalt chloride, cobalt bromide, cobalt hydroxide, cobalt naphthenate, cobalt nitrate, cobalt phosphate, and cobalt sulfate.

Examples of suitable nickel compounds include nickel acetate, nickel formate, nickel acetylacetonate, ammonium nickel sulfate, nickel chloride, nickel bromide, nickel carbonate, nickel hydroxide, nickel naphthenate, nickel nitrate, potassium nickel cyanide, and nickel sulfate.

Examples of suitable zinc compounds include zinc acetate, zinc benzoate, zinc lactate, zinc chloride, zinc bromide, zinc iodide, zinc carbonate, zinc nitrate, zinc phosphate, and zinc sulfate.

Examples of suitable lead compounds include lead acetate, lead tetraacetate, lead citrate, lead oxalate, lead chloride, lead iodide, lead carbonate, lead borate, lead metaborate, lead nitrate, and lead sulfate.

The metallic compound is used in an amount of from 0.0001 to 5 mol %, preferably from 0.0005 to 2.5 mol %, and more preferably from 0.001 to 1.0 mol %, based on the starting aromatic hydrocarbon.

The manner of addition of the metallic compound is not particularly restricted, and it may be added all at once at the commencement of the reaction, or continuously during the reaction, or in divided portions at regular intervals.

The reaction system preferably contains, as an additive, ammonia, an ammonium salt, or a substance which decomposes in the reaction system to release ammonia.

Examples of ammonia or ammonium salts include ammonia gas, aqueous ammonia of an arbitrary concentration; inorganic ammonium salts, e.g., ammonium sulfate, ammonium hydrochloride, ammonium nitrate, ammonium borate, ammonium hydrogencarbonate, and ammonium hydrogensulfate; and organic ammonium salts, e.g., ammonium formate, ammonium acetate, and ammonium citrate (($NH_4)_3C_6H_5O_7$, $(NH_4)_2HC_6H_5O_7$; and $NH_4H_2C_6H_5O_7$).

Examples of the substance which decomposes in the reaction system to release ammonia include urea, methylurea, 1,1-dimethylurea, 1,3-dimethylurea, cyanuric acid, isocyanuric acid, melamine, biuret, biurea, and primary amines.

The ammonia, ammonium salt or substance capable of releasing ammonia is added in an amount of from 0.01 to 300 mol %, preferably from 0.1 to 150 mol %, and more preferably from 1 to 50 mol %, based on the starting aromatic hydrocarbon.

If desired, the reaction system may further contain a surface active agent. The surface active agent to be added is not particularly limited and includes, for example, fatty acid soaps, alkyl sulfonates, alkylbenzenesulfonates, alkylnaphthalenesulfonates, alkyl ether sulfonates, alkylphosphates, and alkyl ether phosphates. These surface active agents may be used either individually or as a mixture of two or more thereof at an arbitrary mixing ratio.

Where a surface active agent is used, it is added in an amount of from 0.001 to 5% by weight, and preferably from 0.01 to 2% by weight, based on the starting aromatic hydrocarbon.

Molecular oxygen which is used for oxidation includes oxygen gas and air. Oxygen gas may be used as diluted with an inert gas, e.g., nitrogen, argon, and helium, to an arbitrary concentration. It should be noted that pure oxygen is preferred where the oxidation reaction is performed under pressure in an apparatus with no vent for a gaseous phase. When air or diluted oxygen is used, it is advantageous to make up for the consumed oxygen by pure oxygen. Where the reaction is conducted under pressure in a vented apparatus, it is economically advantageous to use air.

For the purpose of shortening the induction period of the oxidation reaction, a radical initiator is preferably used. Examples of suitable radical initiators include 2,2'-azobis-isobutyronitrile, 1,1'-azobis(cyclohexane-1-carbonitrile), cumene hydroperoxide, and t-butyl hydroperoxide. The oxidation product containing a hydroperoxide of the aromatic hydrocarbon having two or more secondary alkyl groups per molecule may be used for that purpose.

The radical initiator is used in an amount of from 0.005 to 1% by weight based on the starting aromatic hydrocarbon.

The oxidation reaction is carried out by feeding molecular oxygen to a reaction system consisting of the basic aqueous solvent, the starting aromatic hydrocarbon, the metal ion source and, if desired, ammonia, an ammonium salt or a substance which decomposes in the reaction system to release ammonia, a surface active agent, a radical initiator, etc. while stirring.

The reaction temperature ranges from 60° to 150° C., and preferably from 80° to 130° C. If the temperature is less than 60° C., the reaction rate is considerably low. At temperatures higher than 150° C., decomposition of the hydroperoxide group is significantly accelerated.

The reaction is either under normal pressure or under pressure, and under a pressure of from normal pressure up to 10 kg/cm$^2$G for preference.

The reaction time usually ranges from 4 to 48 hours, though varying depending on the reaction temperature, presence or absence of a radical initiator, and other factors.

The polyhydroperoxide compounds which are produced according to the process of the present invention include m- or p-bis(2-hydroperoxy-2-propyl)benzene, 2,6- or 2,7-bis(2-hydroperoxy-2-propyl)naphthalene, and 4,4'-bis(2-hydroperoxy-2-propyl)biphenyl.

The present invention is now illustrated in greater detail by way of Examples, but it should be understood that the present invention is not deemed to be limited thereto.

In Examples, all the percents are by weight unless otherwise indicated.

Yields of the products obtained were calculated according to equation:

$$\text{Yield (mol \%)} = \frac{\text{Mole number of product}}{\text{Mole number of starting aromatic hydrocarbon}} \times 100$$

Conversions of the secondary alkyl groups were calculated according to equation:

$$\text{Conversion (mol \%)} = \frac{\text{Mole number of secondary alkyl groups reacted}}{\text{Mole number of secondary alkyl groups in starting aromatic hydrocarbon}} \times 100$$

Composition analysis and quantitative determination were conducted by high performance liquid chromatography.

EXAMPLE 1

In a 50 ml-volume autoclave made of SUS 316 (iron content: about 70%) were charged 7.15 g (30.0 mmol) of 4,4'-diisopropylbiphenyl (hereinafter abbreviated as DIPBP), 18.0 g (0.9 mmol) of a 0.2% aqueous solution of sodium hydroxide, 0.2 g of 25% aqueous ammonia, 0.038 g of a surface active agent "Nonsal LN-1" (a mixture of saturated aliphatic carboxylic acid sodium salts, produced by Nippon Oils & Fats Co., Ltd.), 10 mg of 2,2'-azobisisobutyronitrile as a radical initiator, and 0.149 mg ($6 \times 10^{-4}$ mmol) of cobalt acetate tetrahydrate.

Oxygen was introduced into the autoclave under a pressure of 3 kg/cm$^2$GF, and the reaction mixture was stirred at 1500 rpm at 100° C. for 14 hours to conduct oxidation while continuously feeding oxygen so as to maintain the reaction pressure at 3 kg/cm$^2$G. During the reaction, a 0.149 mg ($6 \times 10^{-4}$ mmol) portion of cobalt acetate tetrahydrate was added every 2 hours. The cobalt acetate tetrahydrate added totaled up to 1.043 mg ($4.2 \times 10^{-3}$ mmol), which corresponded to 0.014 mol % based on DIPBP.

The DIPBP conversion was 99.2 mol %, and the yield of 4,4'-bis(2-hydroperoxy-2-propyl)biphenyl was 41.4 mol %. In addition, 4-(2-hydroxy-2-propyl)-4,-(2-hydroperoxy-2-propyl)-biphenyl, 4,4'-bis(2-hydroxy-2-propyl)biphenyl, 4-(2-hydroperoxy-2-propyl)-4,-isopropylbiphenyl, and 4-(2-hydroxy-2-propyl)-4,-isopropylbiphenyl were produced in yields of 31.3 mol %, 5.8 mol %, 10.3 mol %, and 4.3 mol %, respectively. The conversion of the isopropyl groups was 91.9 mol %.

EXAMPLE 2

In a 50 ml-volume autoclave made of SUS 316 were charged 7.15 g (30.0 mmol) of DIPBP, 18.0 g (0.9 mmol) of a 0.2% aqueous solution of sodium hydroxide, 0.2 g (3.0 mmol) of 25% aqueous ammonia, 0.036 g of "Nonsal LN-1", 10 mg of 2,2'-azobisisobutyronitrile, bisisobutyronitrile, and 1.485 mg ($6 \times 10^{-3}$ mmol) of nickel acetate tetrahydrate.

Oxygen was introduced into the autoclave under a pressure of 3 kg/cm$^2$G, and the reaction mixture was stirred at 1500 rpm at 100° C. for 14 hours to conduct oxidation while continuously feeding oxygen so as to maintain the reaction pressure at 3 kg/cm$^2$G. During the reaction, a 1.485 mg ($6 \times 10^{-3}$ mmol) portion of nickel acetate tetrahydrate was added every 2 hours. The nickel acetate tetrahydrate added totaled up to 10.359 mg ($4.2 \times 10^{-2}$ mmol), which corresponded to 0.14 mol % based on DIPBP.

The DIPBP conversion was 99.2 mol %, and the yield of 4,4'-bis(2-hydroperoxy-2-propyl)biphenyl was 50.9 mol %. In addition, 4-(2-hydroxy-2-propyl)-4'-(2-hydroperoxy-2-propyl)-biphenyl, 4,4'-bis(2-hydroxy-2-propyl)biphenyl, 4-(2-hydroperoxy-2-propyl)-4'-isopropylbiphenyl, and 4-(2-hydroxy-2-propyl)-4'-isopropylbiphenyl were produced in yields of 24.9 mol %, 3.4 mol %, 12.5 mol %, and 3.5 mol %, respectively. The conversion of the isopropyl groups was 91.2 mol %.

EXAMPLE 3

In a 50 ml-volume autoclave made of SUS 316 were charged 7.15 g (30.0 mmol) of DIPBP, 18.0 g (0.9 mmol) of a 0.2% aqueous solution of sodium hydroxide, 0.2 g (3.0 mmol) of 25% aqueous ammonia, 0.036 g of "Nonsal LN-1", 10 mg of 2,2'-azobisisobutyronitrile, and 0.659 mg ($3 \times 10^{-3}$ mmol) of zinc acetate dihydrate.

Oxygen was introduced into the autoclave under a pressure of 3 kg/cm$^2$G, and the reaction mixture was stirred at 1500 rpm at 100° C. for 8 hours to conduct oxidation while continuously feeding oxygen so as to maintain the reaction pressure at 3 kg/cm$^2$G. During the reaction, a 0.659 mg ($3 \times 10^{-3}$ mmol) portion of zinc acetate dihydrate was added every 2 hours. The zinc acetate dihydrate added totaled up to 2.636 mg ($1.2 \times 10^{-2}$ mmol), which corresponded to 0.04 mol % based on DIPBP.

The DIPBP conversion was 98.6 mol %, and the yield of 4,4'-bis(2-hydroperoxy-2-propyl)biphenyl was 45.3 mol %. In addition, 4-(2-hydroxy-2-propyl)-4'-(2-hydroperoxy-2-propyl)biphenyl, 4,4'-bis(2-hydroxy-2-propyl)biphenyl, 4-(2-hydroperoxy-2-propyl)-4'-isopropylbiphenyl, and 4-(2-hydroxy-2-propyl)-4'-isopropylbiphenyl were produced in yields of 25.2 mol %, 3.4 mol %, 14.6 mol %, and 4.8 mol %, respectively. The conversion of the isopropyl groups was 88.9 mol %.

EXAMPLE 4

In a 50 ml-volume autoclave made of SUS 316 were charged 7.15 g (30.0 mmol) of DIPBP, 18.0 g (0.9 mmol) of a 0.2% aqueous solution of sodium hydroxide, 0.2 g (3.0 mmol) of 25% aqueous ammonia, 0.036 g of "Nonsal LN-1", 10 mg of 2,2'-azobisisobutyronitrile, and 2.276 mg ($6 \times 10^{-3}$ mmol) of lead acetate trihydrate.

Oxygen was introduced into the autoclave under a pressure of 3 kg/cm$^2$G, and the reaction mixture was stirred at 1500 rpm and at 100° C. for 10 hours to conduct oxidation while continuously feeding oxygen so as to maintain the reaction pressure at 3 kg/cm$^2$G. During the reaction, a 2.276 mg ($6 \times 10^{-3}$ mmol) portion of lead acetate trihydrate was added every 2 hours. The lead acetate trihydrate added totaled up to 11.38 mg ($3.0 \times 10^{-2}$ mmol), which corresponded to 0.1 mol % based on DIPBP.

The DIPBP conversion was 96.5 mol %, and the yield of 4,4'-bis(2-hydroperoxy-2-propyl)biphenyl was 37.8 mol %. In addition, 4-(2-hydroxy-2-propyl)-4'-(2-hydroperoxy-2-propyl)biphenyl, 4,4'-bis(2-hydroxy-2-propyl)biphenyl, 4-(2-hydroperoxy-2-propyl)-4'-isopropylbiphenyl, and 4-(2-hydroxy-2-propyl)-4'-isopropylbiphenyl were produced in yields of 22.5 mol %, 3.2 mol %, 22.3 mol %, and 6.9 mol %, respectively.

The conversion of the isopropyl groups was 81.9 mol %.

COMPARATIVE EXAMPLE 1

Oxidation of DIPBP was carried out in the same manner as in Example 1, except for using no cobalt acetate.

The DIPBP conversion was 82.5 mol %, and the yield of 4,4'-bis(2-hydroperoxy-2-propyl)biphenyl was 27.9 mol %. In addition, 4-(2-hydroxy-2-propyl)-4'-(2-hydroperoxy-2-propyl)biphenyl, 4,4'-bis(2-hydroxy-2-propyl)biphenyl, 4-(2-hydroperoxy-2-propyl)-4'-isopropylbiphenyl, and 4-(2-hydroxy-2-propyl)-4'-isopropylbiphenyl were produced in yields of 7.1 mol %, 0.44 mol %, 38.7 mol %, and 6.5 mol %, respectively. The conversion of the isopropyl groups was 59.9 mol %.

EXAMPLE 5

In a 50 ml-volume autoclave made of SUS 316 were charged 6.37 g (30.0 mmol) of 2,6-diisopropylnaphthalene (hereinafter abbreviated as DIPN), 18.0 g (0.9 mmol) of a 0.2% aqueous solution of sodium hydroxide, 0.2 g (3.0 mmol) of 25% aqueous ammonia, 0.036 g of "Nonsal LN-1", 10 mg of 2,2'-azobisisobutyronitrile, and 1.485 mg ($6 \times 10^{-3}$ mmol) of nickel acetate tetrahydrate.

Oxygen was introduced into the autoclave under a pressure of 3 kg/cm$^2$G, and the reaction mixture was stirred at 1500 rpm and at 100° C. for 8 hours to conduct oxidation while continuously feeding oxygen so as to maintain the reaction pressure at 3 kg/cm$^2$G. During the reaction, a 1.485 mg ($6 \times 10^{-3}$ mmol) portion of nickel acetate tetrahydrate was added every 2 hours. The nickel acetate tetrahydrate added totaled up to 5.94 mg ($2.4 \times 10^{-2}$ mmol), which corresponded to 0.08 mol % based on DIPN.

The DIPN conversion was 92.8 mol %, and the yield of 2,6-bis(2-hydroperoxy-2-propyl)naphthalene was 33.4 mol %. In addition, 2-(2-hydroxy-2-propyl)-6-(2-hydroperoxy-2-propyl)-naphthalene, 2,6-bis(2-hydroxy-2-propyl)naphthalene, 2-(2-hydroperoxy-2-propyl)-6-isopropylnaphthalene, and 2-(2-hydroxy-2-propyl)-6-isopropylnaphthalene were produced in yields of 19.1 mol %, 3.3 mol %, 25.2 mol %, and 8.9 mol %, respectively. The conversion of the isopropyl groups was 75.8 mol %.

COMPARATIVE EXAMPLE 2

Oxidation of DIPN was carried out in the same manner as in Example 5, except for using no nickel acetate.

The DIPN conversion was 89.6 mol %, and the yield of 2,6-bis(2-hydroperoxy-2-propyl)naphthalene was 29.7 mol %. In addition, 2-(2-hydroxy-2-propyl)-6-(2-hydroperoxy-2-propyl)-naphthalene, 2,6-bis(2-hydroxy-2-propyl)naphthalene, 2-(2-hydroperoxy-2-propyl)-6-isopropylnaphthalene, and 2-(2-hydroxy-2-propyl)-6-isopropylnaphthalene were produced in yields of 11.9 mol %, 1.2 mol %, 35.3 mol %, and 7.9 mol %, respectively. The conversion of the isopropyl groups was 67.9 mol %.

According to the process of the present invention characterized in that a specific metal ion is present in the reaction system, the phenomenon that the oxidation reaction virtually stops in its course, failing to obtain an increased conversion of secondary alkyl groups, which phenomenon has been conventionally associated with the use of an apparatus made of an iron-containing metal, can be eliminated. Thus, even in using an apparatus made of an iron-containing metal generally employed in production industry, a high conversion of secondary alkyl groups can be reached, and the desired polyhydroperoxide can be obtained in a high yield.

While the invention has been described in detail and with reference to specific examples thereof, it will be apparent to one skilled in the art that various changes and modifications can be made therein without departing from the spirit and scope thereof.

What is claimed is:

1. A process for preparing a polyhydroperoxy aromatic compound which comprises reacting a polysecondary alkylsubstituted aromatic hydrocarbon with the secondary alkyl groups on carbon atoms that are not adjacent to each other on the aromatic ring thereof with a molecular oxygencontaining gas in a basic aqueous solvent in the presence of a surface active agent, wherein the reaction is conducted in a reaction apparatus whose part in contact with a reaction liquid comprises a metal containing 10% by weight or more of iron, and the reaction is carried out in the presence of a metal ion selected from the group consisting of a cobalt ion, a nickel ion, a zinc ion, and a lead ion.

2. A process as claimed in claim 1, wherein said aromatic hydrocarbon contains from 1 to 8 aromatic rings.

3. A process as claimed in claim 1, wherein said aromatic hydrocarbon has from 2 to 4 secondary alkyl groups.

4. A process as claimed in claim 1, wherein said secondary alkyl groups each have from 3 to 9 carbon atoms.

5. A process as claimed in claim 1, wherein said metal containing iron is selected from carbon steel, stainless steel, cast iron, and Hastelloy A.

6. A process as claimed in claim 1, wherein a metallic compound supplying said metal ion is present in an amount of from 0.0001 to 5 mol % based on said aromatic hydrocarbon.

7. A process as claimed in claim 1, wherein said surface active agent is present in an amount of from 0.001 to 5% by weight based on said aromatic hydrocarbon.

8. A process as claimed in claim 1, wherein said reaction is carried out in the presence of ammonia, an ammonium salt, or a substance which decomposes in the reaction system to release ammonia.

9. A process as claimed in claim 8, wherein said ammonia, ammonium salt or substance which decomposes in the reaction system to release ammonia is present in an amount of from 0.01 to 300% by weight based on said aromatic hydrocarbon.

10. A process as claimed in claim 1, wherein said molecular oxygen is pure oxygen or air.

11. A process as claimed in claim 1, wherein said reaction is carried out at a temperature of from 60° to 150° C.

12. A process as claimed in claim 1, wherein said reaction is carried out under normal pressure or under a pressure up to 10 kg/cm$^2$G.

* * * * *